US009526582B2

United States Patent
Kim et al.

(10) Patent No.: US 9,526,582 B2
(45) Date of Patent: Dec. 27, 2016

(54) ENDOSCOPE ROBOT HAVING JOINT STRUCTURE WITH HIGH CURVATURE

(71) Applicant: KOREA INSTITUTE OF SCIENCE AND TECHNOLOGY, Seoul (KR)

(72) Inventors: Keri Kim, Seoul (KR); Sung Chul Kang, Seoul (KR); Woosub Lee, Seoul (KR); Sangmyung Kim, Seoul (KR); Soojun Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 357 days.

(21) Appl. No.: 14/264,579

(22) Filed: Apr. 29, 2014

(65) Prior Publication Data

US 2015/0223895 A1   Aug. 13, 2015

(30) Foreign Application Priority Data

Feb. 10, 2014  (KR) .......................... 10-2014-0014945

(51) Int. Cl.
*A61B 19/00* (2006.01)
*A61B 1/00* (2006.01)
(Continued)

(52) U.S. Cl.
CPC ......... *A61B 19/2203* (2013.01); *A61B 1/0016* (2013.01); *A61B 1/0051* (2013.01);
(Continued)

(58) Field of Classification Search
CPC ................ A61B 1/0056–1/0057; A61B 1/008; A61B 1/000098
(Continued)

(56) References Cited

U.S. PATENT DOCUMENTS

| 2005/0096502 A1* | 5/2005 | Khalili ................... | A61B 1/018 600/106 |
| 2007/0167680 A1* | 7/2007 | Miyamoto ........... | A61B 1/0055 600/106 |

(Continued)

FOREIGN PATENT DOCUMENTS

| KR | 10-2006-0086620 A | 8/2006 |
| KR | 10-2010-0058084 | 6/2010 |

(Continued)

OTHER PUBLICATIONS

Yamashita, Hiromasa, et al. "Miniature bending manipulator for fetoscopic intrauterine laser therapy to treat twin-to-twin transfusion syndrome," *Surgical endoscopy*, vol. 22, No. 2, (published online Jul. 28, 2007), pp. 430-435.

*Primary Examiner* — Matthew J Kasztejna
(74) *Attorney, Agent, or Firm* — NSIP Law

(57) ABSTRACT

An endoscope robot inserted into a duct to perform a predetermined work includes a flexible first tube body, a joint structure coupled to an end of the first tube body, and an end-effector connected to the joint structure so that location and direction of the end-effector are adjusted by the joint structure. The joint structure includes a fixed arm coupled to an end of the first tube body, and a plurality of pivotal arms arranged in order in a row from the fixed arm and pivotally connected to each other. The first tube body curves and linearly moves in the duct to move the end-effector to a working position. The plurality of pivotal arms is pivoted at the working position to adjust location and direction of the end-effector.

10 Claims, 18 Drawing Sheets

(51) Int. Cl.
   *A61B 1/005* (2006.01)
   *A61B 17/00* (2006.01)
(52) U.S. Cl.
   CPC .... *A61B 34/30* (2016.02); *A61B 2017/00345* (2013.01); *A61B 2017/00867* (2013.01); *A61B 2034/305* (2016.02); *A61B 2034/306* (2016.02)
(58) Field of Classification Search
   USPC ................ 600/101, 104–107, 112, 114, 146, 600/170–173, 176
   See application file for complete search history.

(56) References Cited

U.S. PATENT DOCUMENTS

| | | |
|---|---|---|
| 2009/0036734 A1 | 2/2009 | Dunki-Jacobs et al. |
| 2010/0036198 A1* | 2/2010 | Tacchino ............. A61B 1/0014 600/106 |
| 2010/0198232 A1* | 8/2010 | Diolaiti .............. A61B 1/00087 606/130 |
| 2013/0018303 A1 | 1/2013 | Webster et al. |

FOREIGN PATENT DOCUMENTS

| | | |
|---|---|---|
| KR | 10-1101274 B1 | 1/2012 |
| KR | 10-1258779 B1 | 4/2013 |
| KR | 10-1280065 B1 | 6/2013 |
| WO | WO 2006/080604 A1 | 3/2006 |

* cited by examiner

ENDOSCOPE ROBOT HAVING JOINT STRUCTURE WITH HIGH CURVATURE

CROSS-REFERENCE TO RELATED APPLICATION

This application claims priority to Korean Patent Application No. 10-2014-0014945, filed on Feb. 10, 2014, and all the benefits accruing therefrom under 35 U.S.C. §119, the contents of which in its entirety are herein incorporated by reference.

BACKGROUND

1. Field

The present disclosure relates to an endoscope robot having a joint structure with a high curvature, and more particularly, to an endoscope robot for performing a predetermined work by inserting a tube body into a duct in which the degree of freedom motion of a high curvature may be added to an end-effector formed at an end of a tube body.

2. Description of the Related Art

Minimal invasive surgery is a surgical procedure performed by minimizing an incision region without incising the stomach and has advantages in substantially no scar or aftereffect and rapid recovery due to the small incision region. In order to perform the minimal invasive surgery, an endoscope robot for micro surgery should be used, and fabrication and control of relevant equipment are being studied.

As an endoscope robot used for micro surgery, a continuum tube robot, so-called an "active cannula", has been proposed.

FIGS. 1A to 1D show a plurality of tube bodies 10 to 40 of an existing continuum tube robot, and FIG. 2 conceptually shows a continuum tube robot composed of the tube bodies of FIG. 1.

As shown in FIGS. 1A to 1D, each tube body 10 to 40 includes linear portions 11, 21, 31, 41 and curved portions 12, 22, 32, 42 extending from the linear portions with predetermined curvatures.

The tube bodies 10 to 40 may be made of a shape-memory alloy with a super-elastic characteristic and may have different lengths, diameters and curvatures so as to move in an overlapped state.

As shown in FIG. 2, due to the interaction of the tube bodies which move in an overlapped state, a location of an end-effector 50 coupled to the front end of the continuum tube robot may be controlled.

The continuum tube robot controls an operation of a rear end located at an outside 1 of a living body and allows the tube bodies 10 to 40 to rotate and/or translate in parallel so that the front end inserted into a working duct 3 extending into a living body 2 suitably curves according to the shape of the duct 3.

In detail, by using an energy equation, a resultant angle for minimizing the energy of the tube bodies 10 to 40 overlapped with each other and a final location of the end-effector are expected.

Each tube body 10 to 40 has a degree of internal rotation and a degree of internal parallel translation, independent from other tube bodies.

As shown in FIG. 2, by suitably allowing the tube bodies 10 to 40 overlapped with each other to rotate and/or translate in parallel, the tube bodies 10 to 40 may suitably curve according to the shape of the duct 3 into which an instrument is inserted, and the end-effector 50 may be finally located at a desired position.

However, in the existing technique, even though the end-effector 50 may be located at a desired position, the direction of the end-effector 50 may not be locally changed at the corresponding position, which gives a limit in operation.

Generally, the end-effector 50 used for the minimal invasive surgery has a very small size, and thus it is very difficult to mount a motor for direction change or the like directly to the end-effector 50.

SUMMARY

The present disclosure is directed to providing an endoscope robot having a joint structure, which may effectively control a direction of an end-effector with a very small size, which is connected to a front end of a micro tube body.

In one aspect, there is provided an endoscope robot, which is inserted into a duct to perform a predetermined work, the endoscope robot including: a flexible first tube body; a joint structure coupled to an end of the first tube body; and an end-effector connected to the joint structure so that location and direction of the end-effector are adjusted by the joint structure, wherein the joint structure includes: a fixed arm coupled to an end of the first tube body; and a plurality of pivotal arms arranged in order in a row from the fixed arm and pivotally connected to each other, wherein the first tube body curves and linearly moves in the duct to move the end-effector to a working position, and wherein the plurality of pivotal arms is pivoted at the working position to adjust location and direction of the end-effector.

According to an embodiment, the first tube body is rotatable based on a central axis of the first tube body in the longitudinal direction, and the end-effector may move in a front and rear direction by pivoting of the plurality of pivotal arms and move in a vertical and horizontal direction by curving and rotating of the first tube body, thereby allowing three-dimensional location and direction changes.

According to an embodiment, the joint structure may further include: a flexible rod configured to linearly move in a length direction of the first tube body relatively with respect to the first tube body so that one of the plurality of pivotal arms is rotated; and a plurality of link bodies for subordinating the plurality of pivotal arms to each other so that when one pivotal arm is pivoted, other pivotal arms are pivoted accordingly.

According to an embodiment, the first tube body may have a hollow, the rod may extend into the first tube body, among the plurality of pivotal arms, a first pivotal arm joint-connected to the fixed arm may be pivoted with respect to the fixed arm, and when the first pivotal arm is pivoted with respect to the fixed arm, other pivotal arms connected to the first pivotal arm in succession may be pivoted accordingly.

According to an embodiment, the endoscope robot may further include a link arm having one end pivotally connected to an end of the rod and the other end pivotally connected to the first pivotal arm, wherein the rod may extend along a center of the length direction of the first tube body, and wherein the first pivotal arm may be pivoted according to pivoting of the link arm caused by linear movement of the rod.

According to an embodiment, the plurality of pivotal arms may be configured to be pivoted in the same.

According to an embodiment, two pivotal arms disposed adjacent to each other may be directly connected by means of a ball joint.

According to an embodiment, the pivotal arm may have a pin-shaped link connector protruding on a side of the pivotal arm, the link body may be rotatably fit into the link connector, and the pivotal arm and the link body may be fixed by riveting an end of the link connector protruding out of the link body.

According to an embodiment, the first tube body may be a micro tube body made of a super-elastic shape-memory alloy and having a curved portion with a predetermined curvature.

According to an embodiment, the endoscope robot may further include a second tube body having a curved portion with a curvature different from the curved portion of the first tube body and made of a super-elastic shape-memory alloy with a greater diameter in comparison to the first tube body, wherein the first tube body may be inserted into the second tube body, and wherein the first tube body and the second tube body overlapped with each other may be relatively moved to change a curved shape of the first tube body so that the first tube body curves or rotates in the duct.

DETAILED DESCRIPTION

Figure 1A:
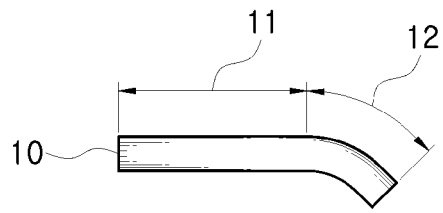
FIGS. 1A to 1D are diagram showing a plurality of tube bodies of an endoscope robot, which is an existing continuum tube robot.
Figure 1B:
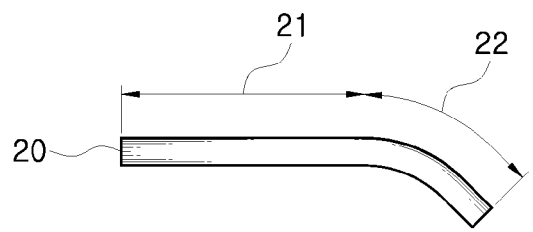
Figure 1C:
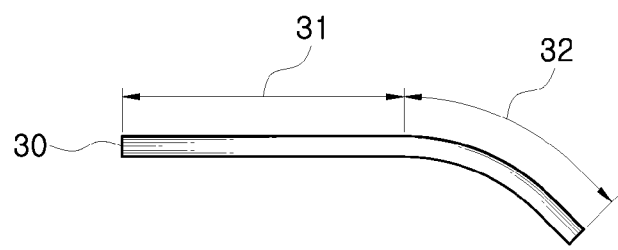
Figure 1D:
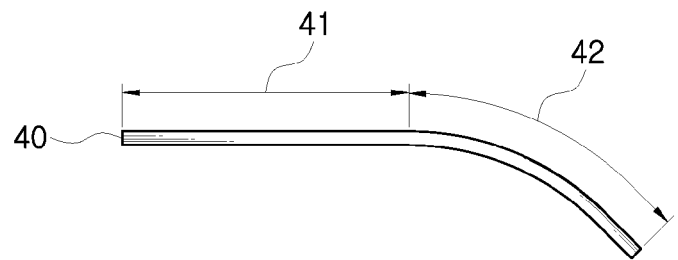
Figure 2:
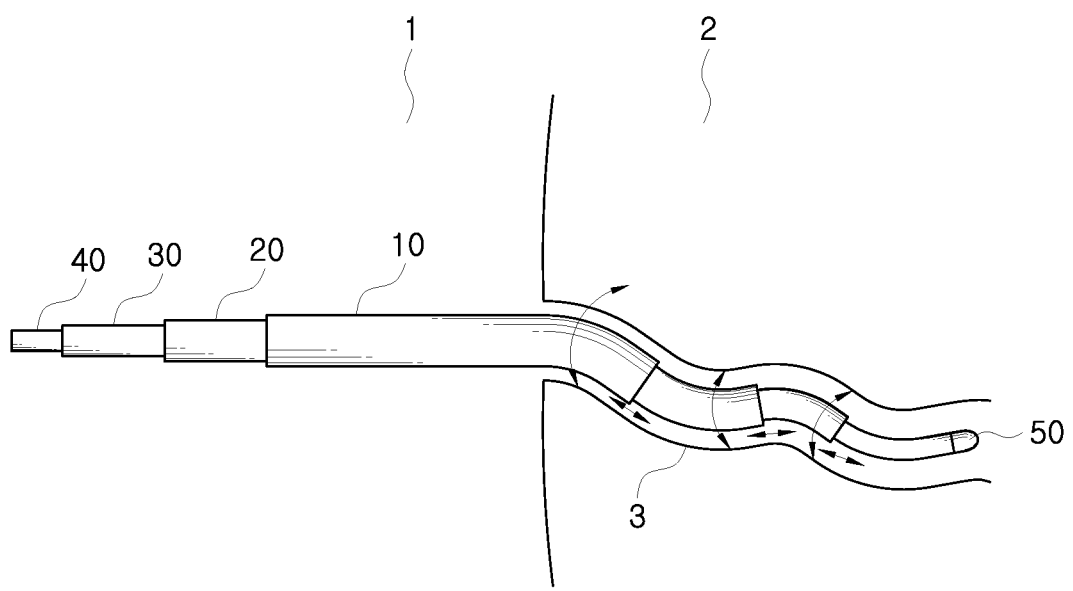
FIG. 2 is a diagram showing an endoscope robot, which is a continuum tube robot composed of the tube bodies of FIG. 1.

Hereinafter, preferred embodiments of the present disclosure will be described with reference to the accompanying drawings. Even though the present disclosure is described based on the embodiments depicted in the drawings, they are just for illustration only, and the technical spirit, essential configuration and operations of the present disclosure are not limited thereto.

Figure 3:
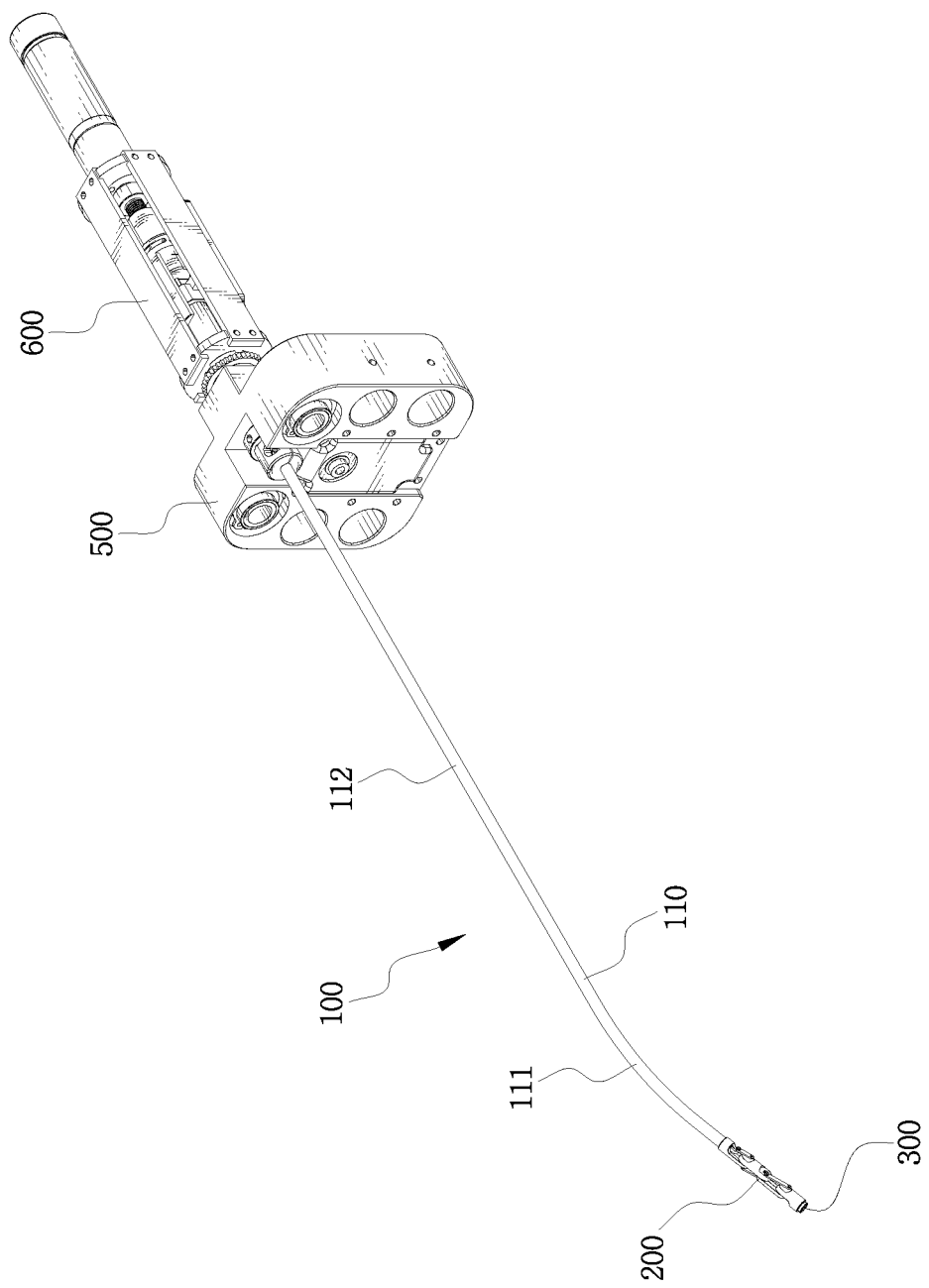
FIG. 3 is a perspective view showing an endoscope robot having a joint structure according to an embodiment of the present disclosure.

FIG. 3 is a perspective view showing an endoscope robot 100 having a joint structure 200 according to an embodiment of the present disclosure.

The "endoscope robot" used in this specification should not be interpreted as being limited to a robot which is inserted into a human body and takes a photograph. The endoscope robot may be one of various kinds of robots which photograph, incise, cut, invade, suture, adhere (weld) or light a work target around an insertion position, or perform various works such as medicine application or administration to the work target.

As shown in FIG. 3, the endoscope robot 100 according to this embodiment includes an elongated hollow first tube body 110, a joint structure 200 connected to a front side of the first tube body 110, an end-effector 300 whose location and direction are adjusted by the joint structure 200, a fixed body 500 for fixing a rear end of the first tube body 110 and an operating device 600 coupled to a rear end of the fixed body 500 to operate the joint structure 200.

The first tube body 110 according to this embodiment may include a linear portion 112 extending linearly, and a curved portion 111 extending from the linear portion 112 and curved with a predetermined curvature.

As described later, the first tube body 110 according to this embodiment configures an innermost tube body with a longest length and a smallest diameter in a continuum tube robot of a so-called "active cannula" (see FIG. 17).

Figure 4:
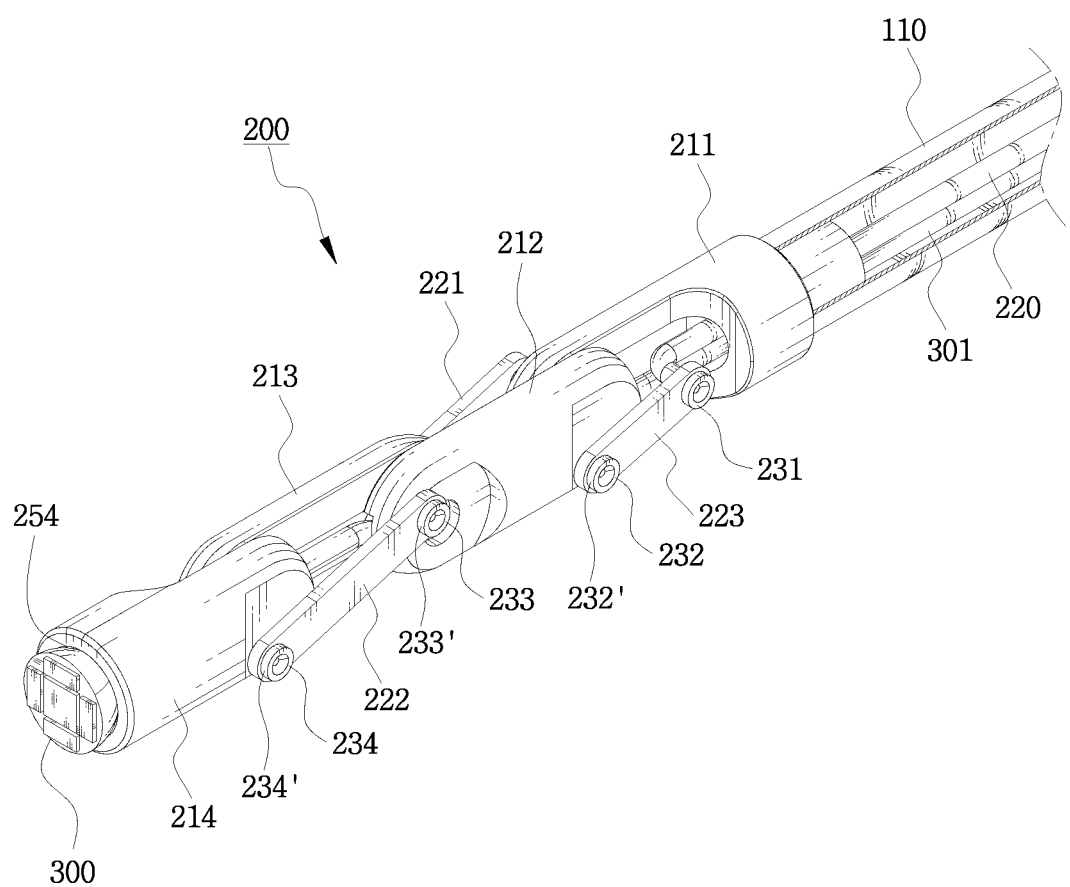
FIG. 4 is an expanded perspective view showing a part of the front end of a working device of FIG. 3.
Figure 5:
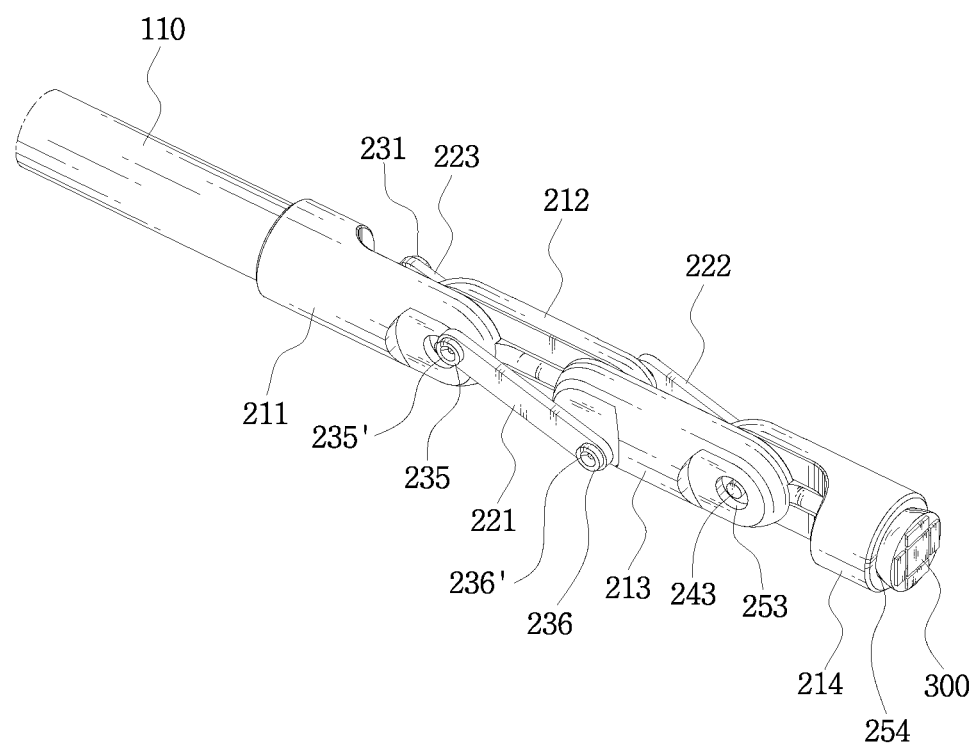
FIG. 5 is an expanded perspective view showing the working device of FIG. 4 at another angle.

FIG. 4 is an expanded perspective view showing a part of the front end of a working device 100 of FIG. 3, and FIG. 5 is an expanded perspective view showing the working device 110 of FIG. 4 at another angle.

Figure 6:
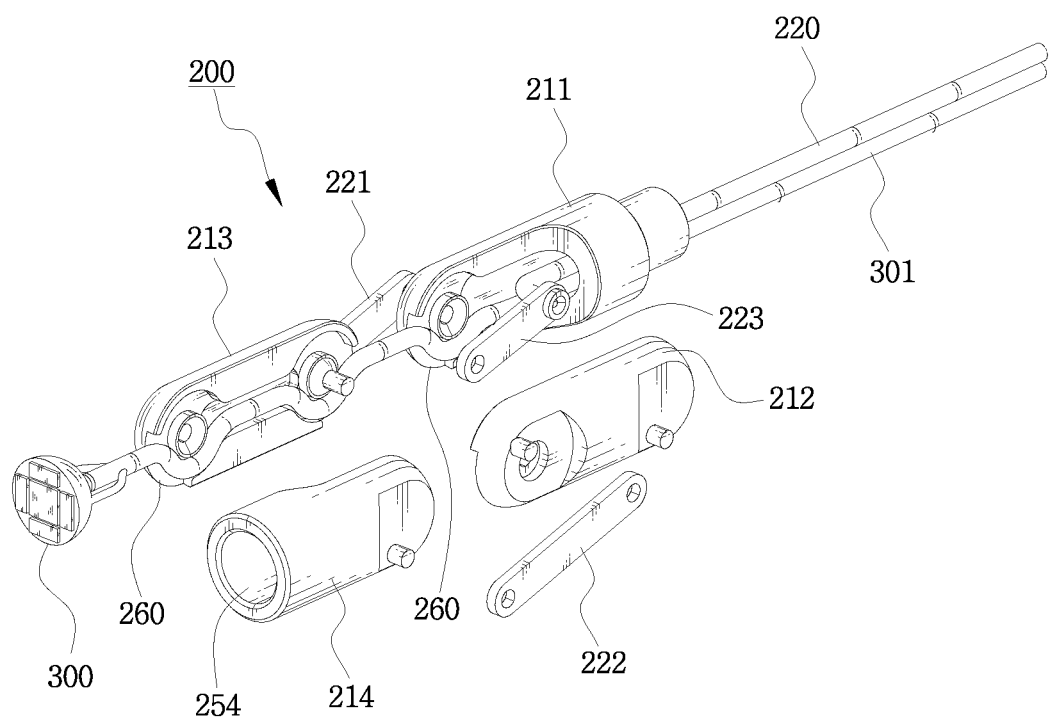
FIG. 6 is an exploded perspective view showing a partial configuration of FIG. 4 separately.

FIG. 6 is an exploded perspective view showing a partial configuration of FIG. 4 separately. In FIG. 6, the first tube body 110 is not depicted.

Figure 7:
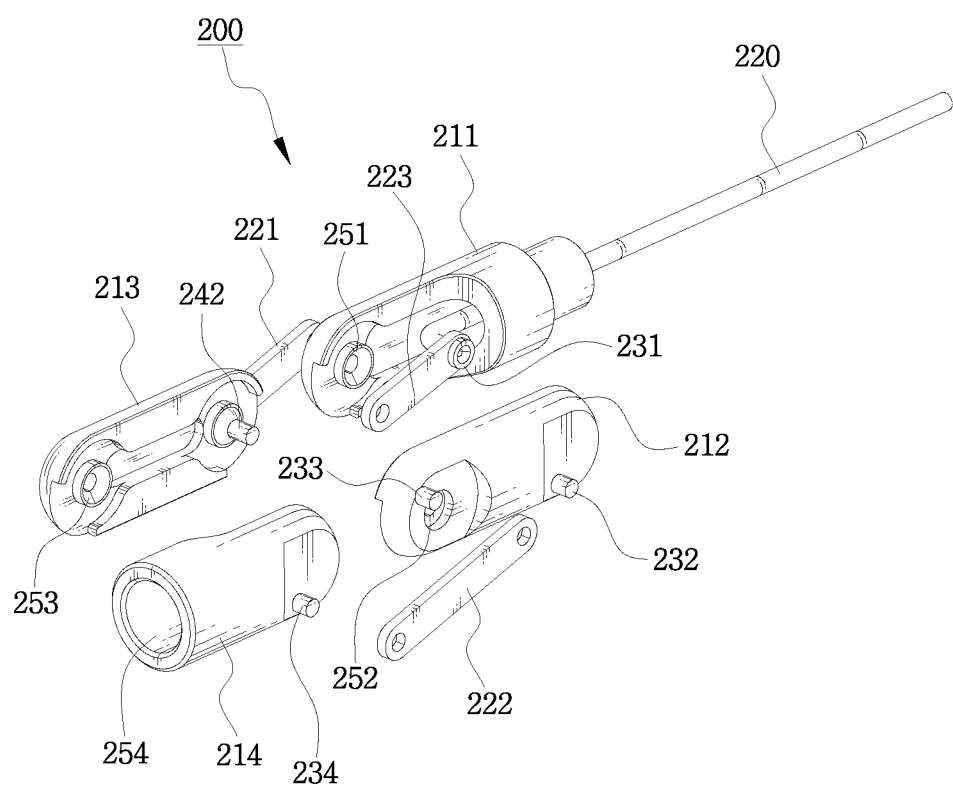
FIG. 7 is an exploded perspective view showing from FIG. 6 from which an end-effector and a cable are excluded.
Figure 8:
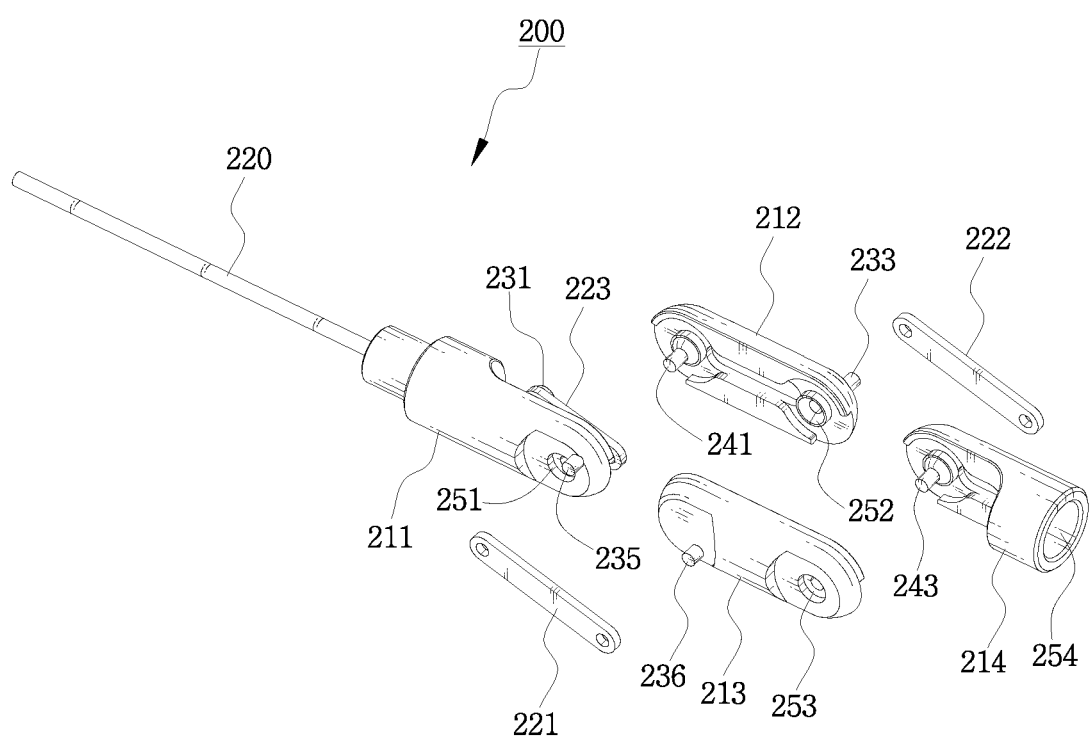
FIG. 8 is an exploded perspective view showing a partial configuration of FIG. 5 separately.

FIG. 7 is an exploded perspective view of FIG. 6 from which an end-effector 300 and a cable 301 are excluded, and FIG. 8 is an exploded perspective view showing a partial configuration of FIG. 5 separately.

As shown in FIGS. 4 to 8, the joint structure 200 according to this embodiment includes a fixed arm 211 fixed to an end of the first tube body 110, and a plurality of pivotal arms 212, 213, 214 arranged in order in a row from the fixed arm 211 and pivotally connected to each other.

The fixed arm 211 and the pivotal arms 212, 213, 214 are shaped by substantially cutting a cylinder partially or entirely in a length direction and connected so that flat cut surfaces come into contact with each other, thereby reducing a size of the joint structure 200 in a lateral direction.

It should be understood that the terms "vertical", "horizontal" and "front and rear" used in this specification do not represent absolute directions of components but are used to define relative location relations among the components.

A first joint connector 251 is formed at the front end of the fixed arm 211, and a ball joint 241 connectable to the first joint connector 251 is provided at the rear end of the first pivotal arm 212. The first pivotal arm 212 is pivotal in the vertical direction with respect to the fixed arm 211 based on the first joint connector 251.

A second joint connector 252 is formed at the front end of the first pivotal arm 212, and a ball joint 242 connectable to the second joint connector 252 is provided at the rear end of the second pivotal arm 213. The second pivotal arm 213 is pivotal in the vertical direction with respect to the first pivotal arm 212 based on the second joint connector 252.

A third joint connector 253 is formed at the front end of the second pivotal arm 213, and a ball joint 243 connectable to the third joint connector 253 is provided at the rear end of the third pivotal arm 214. The third pivotal arm 214 is pivotal in the vertical direction with respect to the second pivotal arm 213 based on the third joint connector 253.

According to this embodiment, due to the degree of freedom of the ball joints 241, 242, 243, the fixed arm 211 and the pivotal arms 212, 213, 214 are joint-connected to be capable of relatively moving with a predetermined gap, and thus when the fixed arm 211 and the pivotal arms 212, 213, 214 are pivoted, the joint structure 200 may operate more softly.

As well shown in FIG. 4, the rod 220 extends through the inside of the first tube body 110, and the front end of the rod 220 is inserted into the fixed arm 211. The rod 220 substantially extends along the center of the first tube body 110 in the length direction.

The rod 220 according to this embodiment is made of flexible material which may curve corresponding to the curve of the flexible first tube body 110. However, the rod 220 is so rigid to move forwards or rearwards in the first tube body 110 to operate the joint structure 200.

The front end of the rod 220 is bent toward the first pivotal arm 212 to form the first link connector 231, and one end of a driving link arm 223 is connected to the first link connector 231 to be pivotal in the vertical direction with respect to the first link connector 231.

The other end of the driving link arm 223 is pivotally connected to a second link connector 232 formed at the outer side of the first pivotal arm 212. The driving link arm 223 is disposed with a downward slope.

A third link connector 233 is formed at the outer side of the front end of the first pivotal arm 212, and a fourth link connector 234 is formed at the outer side of the rear end of the third pivotal arm 214. A first link body 222 is connected to the third link connector 233 and the fourth link connector 234. Both ends of the first link body 222 are pivotal with respect to the link connectors connected thereto.

Similarly, a fifth link connector 235 is formed at the outer side of the front end of the fixed arm 211, and a sixth link connector 236 is formed at the outer side of the rear end of the second pivotal arm 213. A second link body 221 is connected to the fifth link connector 235 and the sixth link connector 236. Both ends of the second link body 221 are pivotal with respect to the link connectors connected thereto.

As shown in FIGS. 6 to 8, before the link bodies 221, 222, 223 are coupled, the link connectors 232 to 236 have a pin shape protruding straightly protruding on the sides of the pivotal arms 212 to 214.

As shown in FIGS. 4 and 5, if the link bodies 221, 222, 223 are inserted into and connected to the corresponding link connectors 231 to 236, a riveting process for beating the link connectors 232 to 236 protruding on the link bodies 221, 222, 223 to form heads 232' to 236' is performed so that the link bodies 221, 222, 223 are rotatably fixed to the corresponding link connectors 231 to 236.

The link structure 200 according to this embodiment is so small to freely adjust a direction of the end-effector in a narrow duct in a human body. Therefore, it is very difficult to fix the link body to the pivotal arm by using a separate coupling device. By fixing the link body to the pivotal arm by means of riveting, it is possible to reduce the size of the link structure 200 and improve the assembling property.

Meanwhile, as well shown in FIG. 6, a cable passage 260 is formed in the flat cut surfaces of the fixed body 211 and the pivotal arms 212, 213, 214 so that a cable 301 connected to the end-effector 300 to supply power to the end-effector 300 and transmit or receive data passes through the cable passage 260.

The cable passage 260 is dimensioned to support the cable 301 and have a predetermined gap with the diameter of the cable 301, so that the pivotal movement of the pivotal arms 212, 213, 214 is not disturbed by the tension of the cable 301.

The end-effector 300 is coupled to the front end of the cable 301, and the end-effector 300 is exposed to a work space through an opening 254 formed at the front end of the third pivotal arm 214.

The end-effector 300 according to this embodiment is a micro camera inserted into the duct to take photographs around an insertion position.

However, the end-effector 300 is not limited to the micro camera but may employ any micro device capable of performing various works in the duct. For example, the end-effector 300 may be a working device which may photograph, incise, cut, invade, suture, adhere (weld) or light a work target around an insertion position, or perform various works such as medicine application or administration to the work target. If an endoscope robot is used for the minimal invasive surgery, small surgery devices such as a camera, a surgical knife, scissors, a syringe or a laser device may be employed.

The cable 301 may serve as a passage which allows a substance such as medicine to flow through the inside thereof and thus supplies the substance to the end-effector 300.

According to this embodiment, if the rod 220 linearly moves in the front and rear direction with respect to the first tube body 110, the first pivotal arm 212 is pivoted in the vertical direction with respect to the fixed arm 211 due to the operation of the driving link arm 223.

As described later, according to this embodiment, due to the restriction of the link bodies 221, 222, movement of the pivotal arms are subordinated to each other so that if one pivotal arm is pivoted, other pivotal arms are also pivoted accordingly. By the operation of the plurality of pivotal arms 212, 213, 214 subordinated to each other, the location and direction of the end-effector 300 coupled to the third pivotal arm 214 at the farthest end are adjusted.

Hereinafter, a configuration for operating the rod 220 and the first tube body 110 will be described first with respect to FIGS. 9 and 10.

Figure 9:
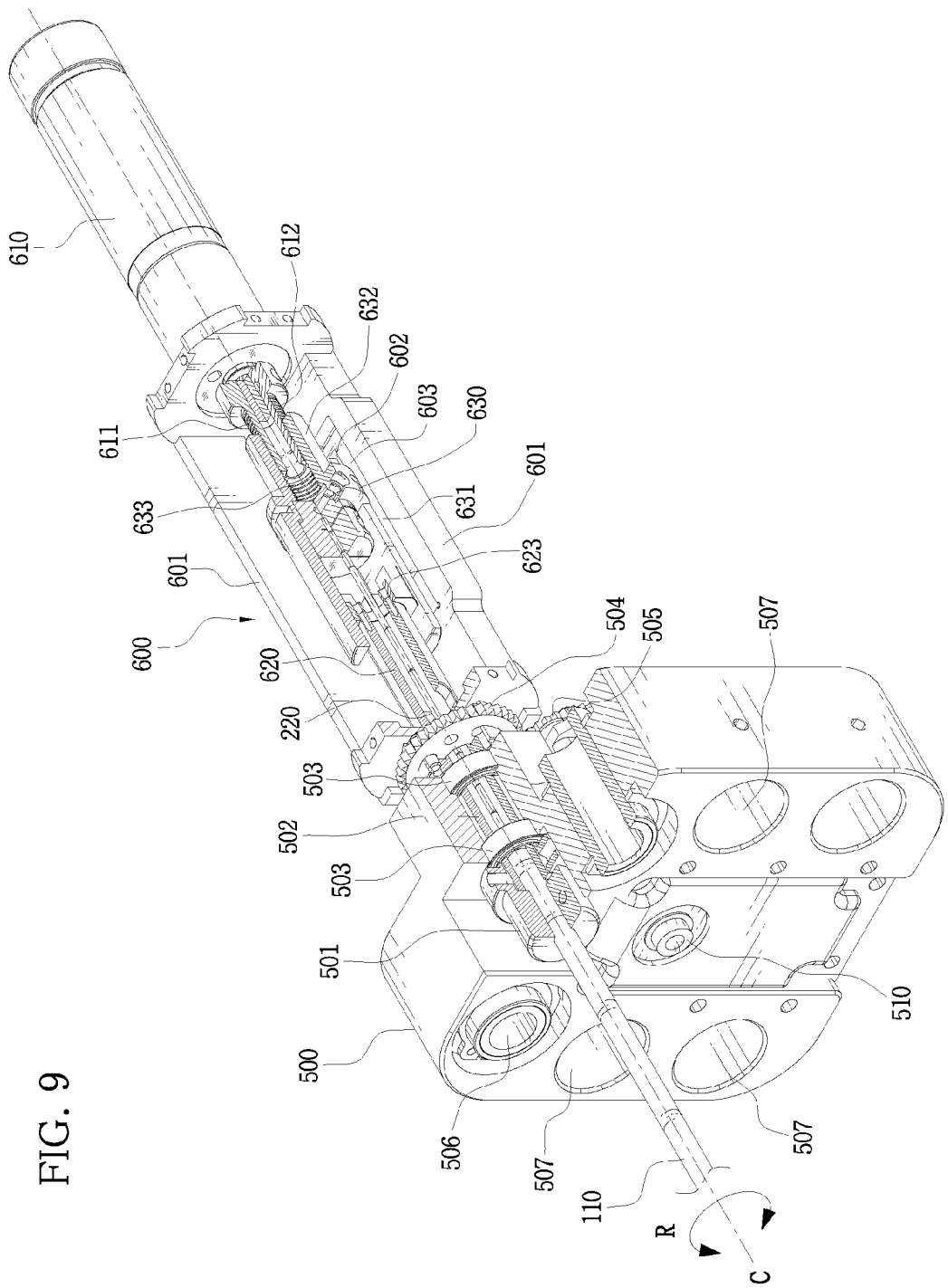
FIGS. 9 and 10 are front and rear perspective views showing the endoscope robot of FIG. 3 from which a partial front configuration is excluded.
Figure 10:
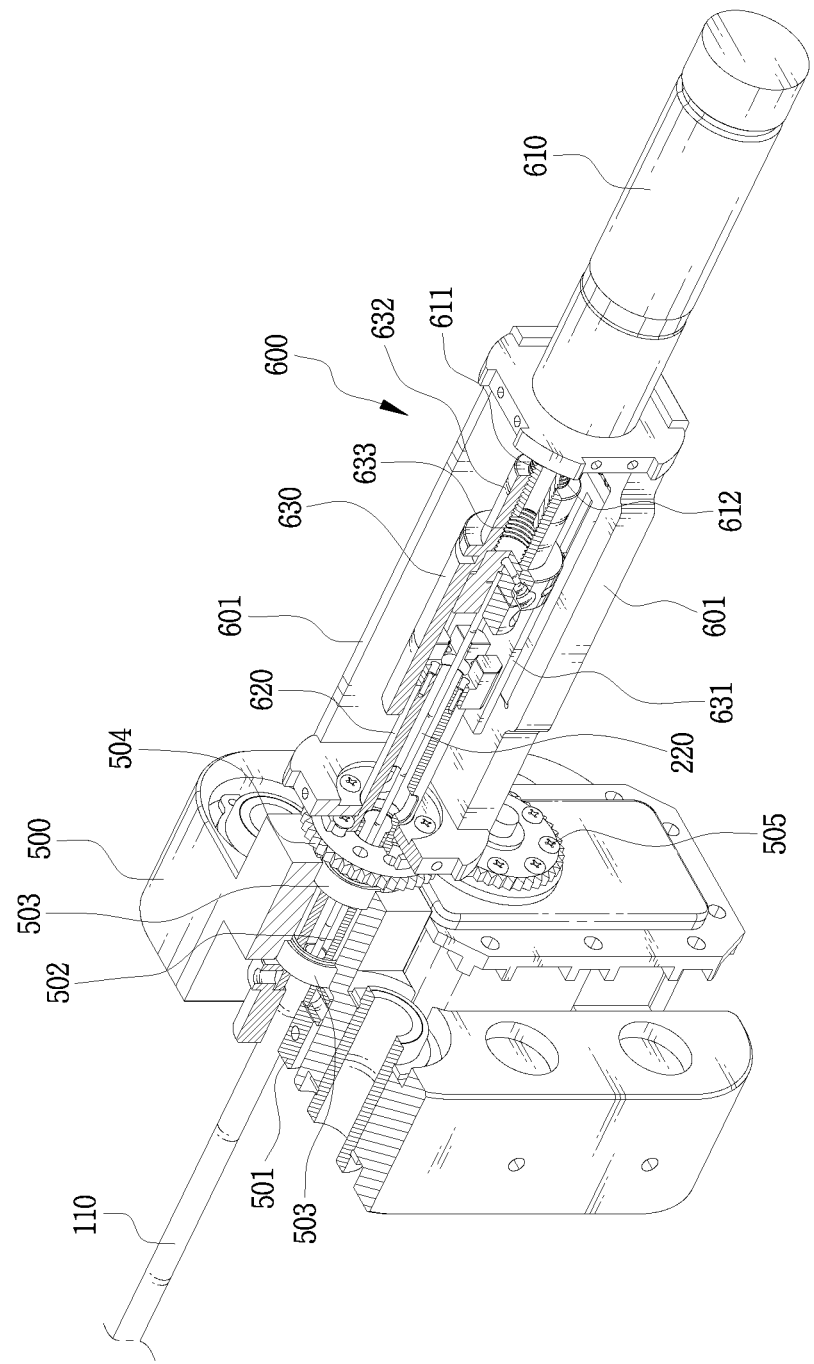

FIGS. 9 and 10 are front and rear perspective views showing the endoscope robot 100, from which a partial front configuration is excluded.

Referring to FIGS. 9 and 10, the fixed body 500 fixes the rear end of the first tube body 110 by a clamp 501. A hollow shaft 502 is fixed to the rear end of the clamp 501, and a first gear 504 is coupled to the rear end of the shaft 502. An operating device 600 is fixed and coupled to the first gear 504.

The first tube body 110, the shaft 502 and the operating device 600 have hollows and communicate with each other so that the rod 220 may pass through them. The first tube body 110 and the operating device 600 are aligned with each other in the length direction.

The shaft 502 is rotatably connected to the fixed body 500 by means of two bearings 503, and the first gear 504 is engaged with a second gear 505 connected to a first motor 510 provided at the fixed body 500.

In this configuration, the rotational force of the first motor 510 allows the first gear 504 to rotate by means of the second gear 505, and the first gear 504 rotates the shaft 502 with respect to the fixed body 500. As the shaft 502 rotates, the first tube body 110 and the operating device 600 rotate simultaneously with respect to the fixed body 500. The first tube body 110 and the operating device 600 are rotated in the circumferential direction R of the central axis of the first tube body 110 in the longitudinal direction C.

The operating device 600 includes a frame 601 rotatably coupled to the fixed body 500, an operating unit located in the frame 601 and connected to the rod 220 to move the rod 220 forwards or rearwards, and a second motor 610 fixed to the rear end of the frame 601 to operate the operating unit.

The operating unit includes a case 620 accommodating the rod 220 and having a front end fixed to the frame 601, a moving bunch 630 located at the rear end of the case 620 and linearly moving along a guide groove 602 formed at the frame 601, and a rotational connector 611 for connecting the linear moving bunch 630 to the second motor 610, in order from the front end.

The moving bunch 630 includes a linear connector 631 fixed to the rear end of the rod 220, and a rotational connector 632 connected to the rear end of the linear connector 631 and having a thread 633 formed at an inner surface thereof.

The rotational connector 632 is connected to the second motor 610 and is screwed with the rotational connector 611 having a thread 612 formed at an outer surface thereof. Therefore, if the second motor 610 rotates, due to an interaction of the rotational connector 632 and the rotational connector 611, the moving bunch 630 moves along the guide groove 602 in the frame 601, thereby making forward and rearward movement.

Though not shown in detail, a position sensor 603 for sensing a position of the moving bunch 630 is provided at the frame 601 to accurately control a forward or rearward location of the moving bunch 630.

Meanwhile, as described later, according to this embodiment, the fixed body 500 is configured to make forward or rearward movement. If the fixed body 500 moves forwards or rearwards, the first tube body 110 fixed thereto moves forwards or rearwards together with the operating device 600 and the rod 220 accommodated in the operating device 600.

In other words, according to this embodiment, if the first tube body 110 moves forwards or rearwards, the rod 220, the moving bodies 310, 320 and the link device 400 must move forwards or rearwards together with the first tube body 110.

Meanwhile, the rod 220 may move forwards or rearwards independently from the first tube body 110 by the rotation of the second motor 610, in a state where the first tube body 110 is fixed.

In addition, as described above, since the first tube body 110 and the operating device 600 may simultaneously rotate with respect to the fixed body 500 by means of the first motor 510, the first tube body 110, the rod 220, the moving bodies 310, 320 and the link device 400 may rotate together based on the central axis C of the first tube body 110.

According to this embodiment, the first pivotal arm 212 joint-connected to the fixed arm 211 is pivoted with respect to the fixed arm 211 by the linear movement of the rod 220, and if the first pivotal arm 212 is pivoted with respect to the fixed arm 211, the pivotal arms 213, 214 connected to the first pivotal arm 212 in succession are also pivoted accordingly. The successive pivotal movement of the plurality of pivotal arms 212, 213, 214 allows the location and direction of the end-effector 300 fixed to the third pivotal arm 214 at the farthest end to be adjusted.

Figure 11A:
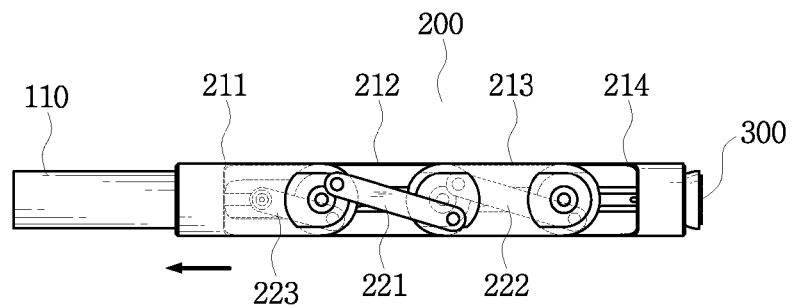
FIGS. 11A to 11C and FIG. 12 are diagrams for illustrating an operation of the joint structure according to an embodiment of the present disclosure.
Figure 11B:
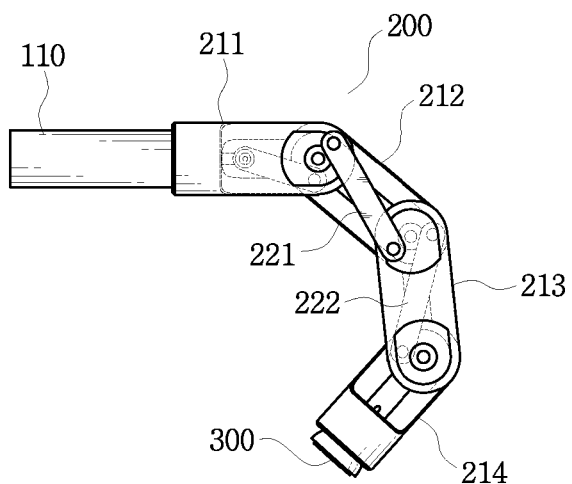
Figure 11C:
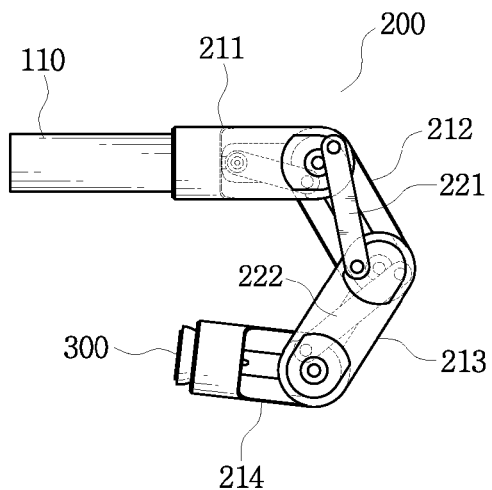
Figure 12:
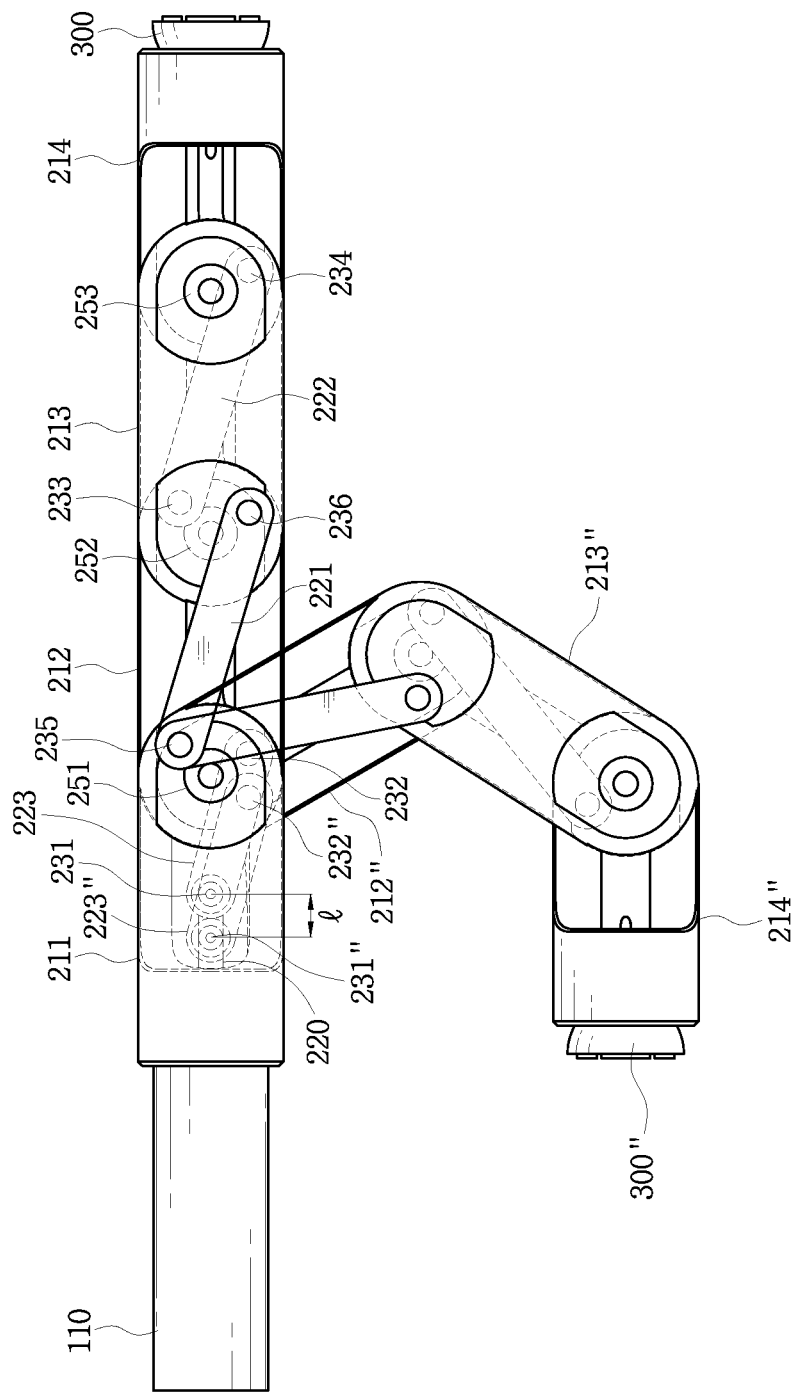

FIGS. 11 and 12 are diagrams for illustrating an operation of the joint structure 200 according to an embodiment of the present disclosure.

As shown in FIGS. 11A to 11C, if the rod 220 moves rearwards toward the first tube body 110 (in the arrow direction of FIG. 11A), the pivotal arms 212, 213, 214 are pivoted in the same direction so that the joint structure 200 is bent as if fingers are bent (FIG. 11A→FIG. 11B→FIG. 11C). On the contrary, if the rod 220 moves forwards in a direction opposite to the first tube body 110, the pivotal arms 212, 213, 214 are pivoted in the same direction so that the joint structure 200 spreads as if fingers spread (FIG. 11C→FIG. 11B→FIG. 11A), thereby adjusting the location and direction of the end-effector 300 connected to the farthest end.

In more detail, with reference to FIG. 12, if the rod 220 moves rearwards so that the first link connector 231 moves rearwards to a location 231" in a state where the joint structure 200 is spread straightly, the driving link arm 223 moves rearwards together and pulls the second link connector 232 to a location 232" so that the first pivotal arm 212 is pivoted downwards with respect to the fixed arm 211 based on the first joint connector 251.

If the first pivotal arm 212 is pivoted downwards, the second pivotal arm 213 connected to the first pivotal arm 212 at the second joint connector 252 also receives a downward force. In addition, the second pivotal arm 213 receives an additional force by the second link body 221 connected to the fifth link connector 235 formed at the fixed arm 211 which is fixed. In detail, the second link body 221 pulls the sixth link connector 236 rearwards so that the second pivotal arm 213 is pivoted downwards with respect to the first pivotal arm 212 based on the second joint connector 252.

If the second pivotal arm 213 is pivoted downwards, the third pivotal arm 214 connected to the second pivotal arm 213 at the third joint connector 253 also receives a downward force. In addition, the third pivotal arm 214 receives an additional force by the first link body 222 connected to the third link connector 233 formed at the first pivotal arm 212. In detail, the first link body 222 pulls the fourth link connector 234 rearwards so that the third pivotal arm 214 is pivoted downwards with respect to the second pivotal arm 213 based on the third joint connector 253.

In other words, if the first pivotal arm 212 is pivoted with respect to the fixed arm 211 by means of the linear movement of the rod 220, the second pivotal arm 213 is pivoted together with the first pivotal arm 212 and also simultaneously pivoted with respect to the first pivotal arm 212, and the third pivotal arm 214 is pivoted together with the second pivotal arm 213 and also simultaneously pivoted with respect to the second pivotal arm 213.

The first pivotal arm 212, the second pivotal arm 213 and the third pivotal arm 214 respectively move to locations 212", 213" and 214" to the maximum, so that the end-effector 300 moving forwards may move rearwards, in a direction entirely opposite to the above, to a location 300".

On the contrary, if the rod 220 moves forwards so that the first link connector 231 moves forwards at a location 231" in a state where the joint structure 200 is entirely bent, the driving link arm 223 moves forwards together and pushes the second link connector 232 so that the first pivotal arm 212 is pivoted upwards with respect to the fixed arm 211 based on the first joint connector 251.

If the first pivotal arm 212 is pivoted upwards, the second pivotal arm 213 connected to the first pivotal arm 212 at the second joint connector 252 also receives an upward force. In addition, the second link body 221 pushes the sixth link connector 236 forwards so that the second pivotal arm 213 is pivoted upwards with respect to the first pivotal arm 212 based on the second joint connector 252.

If the second pivotal arm 213 is pivoted upwards, the third pivotal arm 214 connected to the second pivotal arm 213 at the third joint connector 253 also receives an upward force. In addition, the first link body 222 pushes the fourth link connector 234 forwards so that the third pivotal arm 214 is pivoted upwards with respect to the second pivotal arm 213 based on the third joint connector 253.

By the above operation, the first pivotal arm 212, the second pivotal arm 213 and the third pivotal arm 214 are arranged linearly again so that the end-effector 300 moves forwards.

Figure 13:
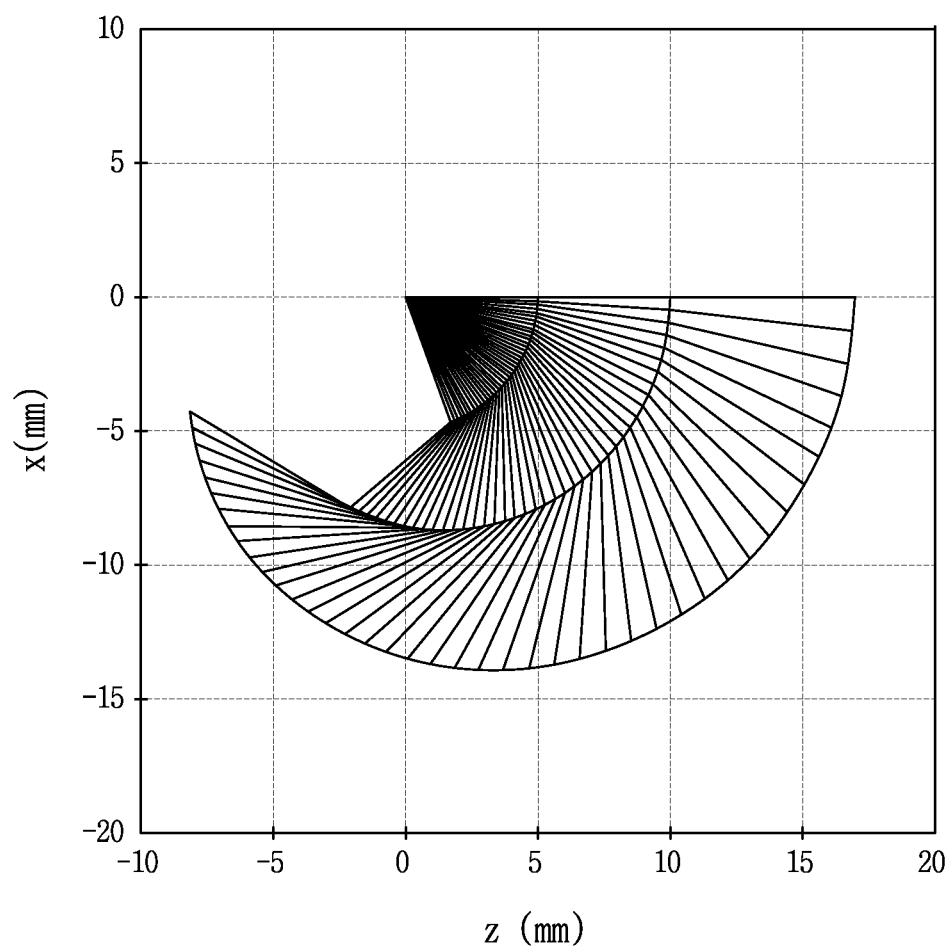
FIG. 13 is a graph showing a trajectory of an end-effector according to an operation of the joint structure.

FIG. 13 shows trajectories of the first pivotal arm 212, the second pivotal arm 213 and the third pivotal arm 214 based on a reference point (0, 0) of the first joint connector 251. In the graph, a trajectory drawing a largest circle at the outermost location represents a trajectory of the end-effector 300.

As shown in FIG. 13, the end-effector 300 moves in the front and rear direction on a two-dimensional x-z plane by the pivotal movement of the plurality of pivotal arms of the joint structure 200.

Figure 14:
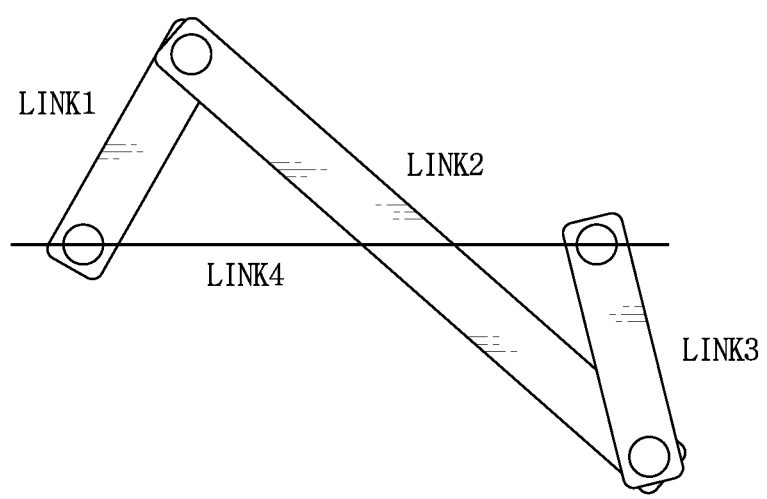
FIGS. 14 and 15 are diagrams for mathematically illustrating an operation of the joint structure according to an embodiment of the present disclosure.
Figure 15:
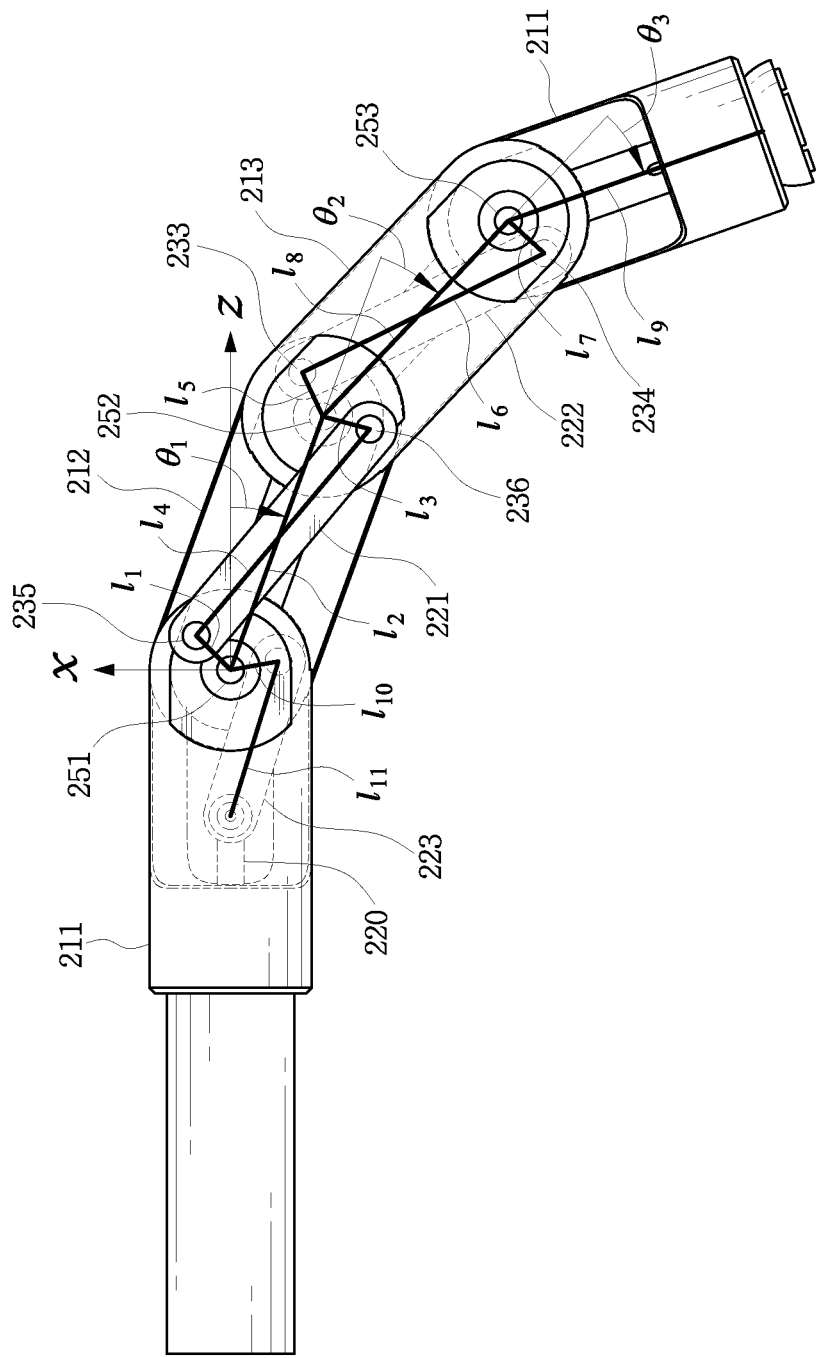

FIGS. 14 and 15 are diagrams for mathematically illustrating an operation of the joint structure 200 according to an embodiment of the present disclosure.

As shown in FIG. 14, the fixed arm 211 and the pivotal arms 212, 213, 214 according to this embodiment configured so that three links, namely Link 1 to Link 3, are connected in an "N" shape, and they are subordinated to each other by means of a four-bar link mechanism in which Link 4 is connected to Link 1 and Link 3.

Therefore, if a rotation angle ($\theta_1$) of the first pivotal arm 212 is determined, a rotation angle ($\theta_2$) of the second pivotal arm 213 and a rotation angle ($\theta_3$) of the third pivotal arm 214 are determined accordingly.

Since the length ($l_{11}$) of the driving link arm 223 and the distance ($l_{10}$) between the second link connector 232 and the first joint connector 251 are already known and the rotation angle ($\theta_1$) of the first pivotal arm 212 is proportional to the linear movement distance (l) of the rod 220 (see FIG. 11), the rotation angle ($\theta_1$) of the first pivotal arm 212 according to the linear movement distance (l) of the rod 220 may be calculated.

In addition, if a distance and relative angle between components are designated as shown in FIG. 5, the location of the end-effector 300 may be expressed as in Equation 1 and Equation 2 below.

$x = l_2 \sin \theta_1 + l_6 \sin(\theta_1 + \theta_2) + l_9 \sin(\theta_1 + \theta_2 + \theta_3)$  Equation 1

$z = l_2 \cos \theta_1 + l_6 \cos(\theta_1 + \theta_2) + l_9 \cos(\theta_1 + \theta_2 + \theta_3)$  Equation 2

According to this embodiment, just by moving the rod 100 forwards or rearwards, the location and direction of the end-effector 300 may be changed with a large curvature. Therefore, since it is not needed to directly mount a motor to the joint structure and operate the end-effector 300, the present disclosure may be suitably used for a tube-insertion endoscope robot with a very small size.

Figure 16:
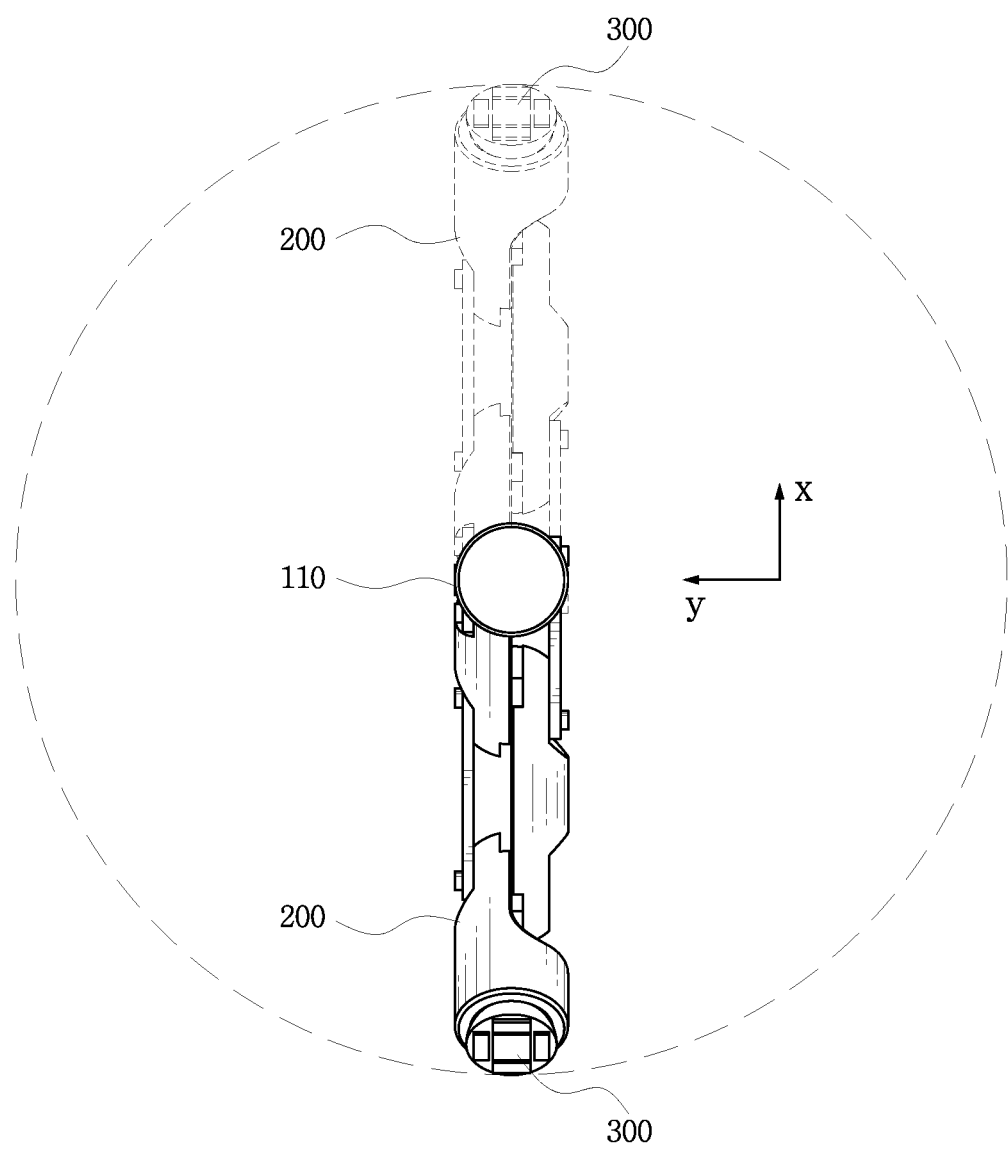
FIG. 16 is a diagram for illustrating an operation of the end-effector according to an operation of a first tube body.

The end-effector 300 according to this embodiment may change a direction along the y axis by rotating the first tube body 110 based on the center of the length direction so that the joint structure 200 and the end-effector 300 rotate together with the first tube body 110. FIG. 16 depicts the end-effector 300 moving while drawing a circular trajectory by the rotation of the first tube body 110.

Meanwhile, according to an embodiment of the present disclosure, for easier access to an organ in the human body, the first tube body 110 is selected as an innermost tube body, and the second tube body 120 serving as a micro tube body having a greater diameter and made of a super-elastic shape-memory alloy with a different curvature may be inserted therein, thereby configuring an "active cannula".

The active cannula is an endoscope instrument for micro surgery, well known in the art, and is disclosed in US Unexamined Patent Publication No. 2013/0018303 or the like.

The active cannula is made of a super-elastic shape-memory alloy with a curvature and is configured to move tube bodies having different diameters and curvatures to be overlapped with each other and adjust a location of the end-effector according to an input angle due to an interaction of the tube bodies.

By using an energy equation, a resultant angle for minimizing the energy possessed by tube bodies overlapped with each other and a final location of the end-effector are expected. Each tube body has a degree of internal rotation and a degree of internal parallel translation, independent from other tube bodies.

By suitably allowing the tube bodies overlapped with each other to rotate and/or translate in parallel, the tube bodies may suitably curve according to the shape of a space into which an instrument is inserted, and the end-effector may be finally located at a desired position.

Figure 17:
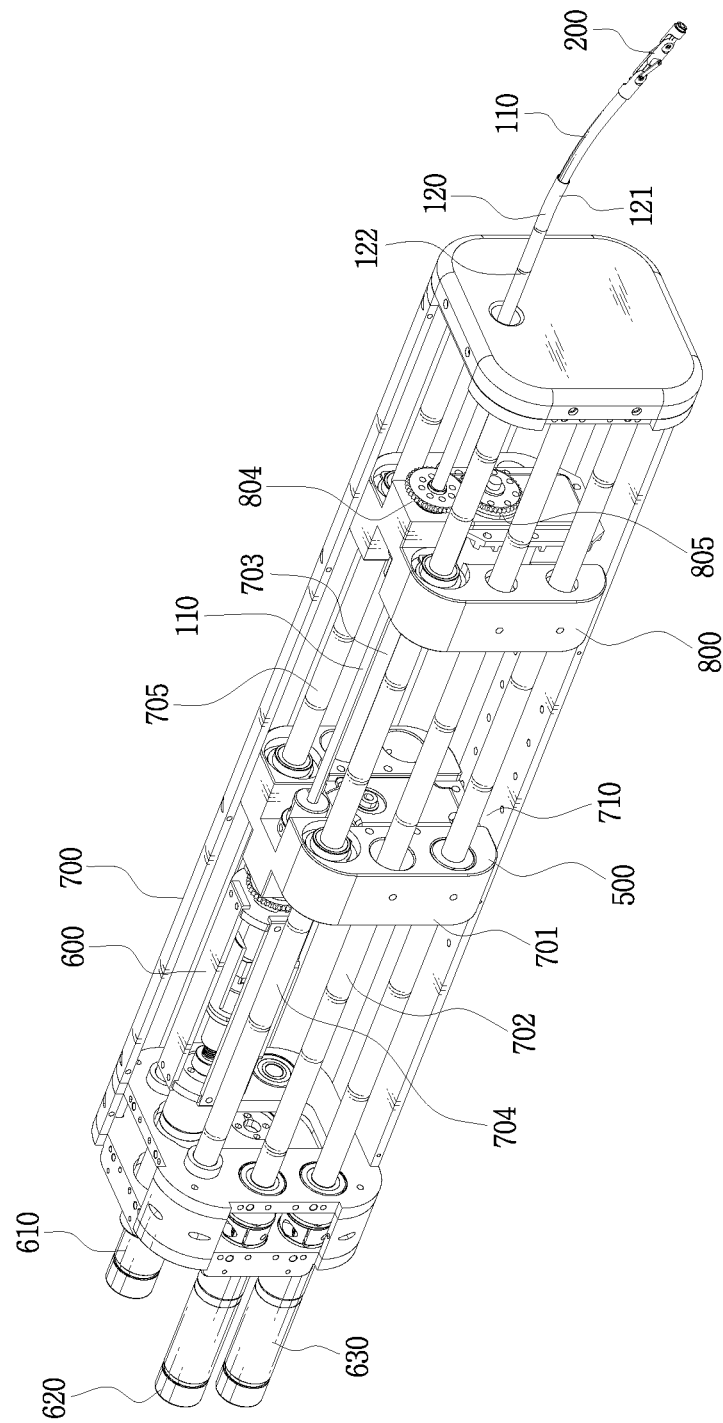
FIG. 17 is a diagram showing an active cannula to which the configuration of FIG. 3 is applied.

FIG. 17 is a diagram showing an active cannula to which the endoscope robot described above is applied.

As shown in FIG. 17, the first tube body 110 is inserted into the second tube body 120 having a greater diameter and a different curvature. The length of the second tube body 120 is shorter than the length of the first tube body 110.

As shown in FIG. 17, the second tube body 120 may include a linear portion 122 extending linearly, and a curved portion 121 extending from the linear portion 122 and curved with a predetermined curvature.

The rear end of the second tube body 120 is fixed to the second fixed body 800. The rear end of the first tube body 110 passes the second fixed body 800 through the rear end of the second tube body 120 and is fixed to the fixed body 500.

The second fixed body 800 may rotate the second tube body 120 based on its longitudinal axis through gears 804, 805 rotated by a motor (not shown), similar to the fixed body 500 described above.

In this configuration, the fixed body 500 and the second fixed body 800 may rotate the first tube body 110 and the second tube body 120 independently.

In addition, a plurality of horizontal bars 701 to 705 are formed at the frame 700 in its length direction, and the plurality of horizontal bars 701 to 705 extend through the through holes 506 and 507 (see FIG. 10) formed in the fixed body 500 and the second fixed body 800.

Among the horizontal bars, the horizontal bars 703, 704, 705 are used for aligning the fixed bodies, and the other horizontal bars 701, 702 are used for moving the fixed body 500 and the second fixed body 800 forwards or rearwards.

As shown in FIG. 17, a third motor and fourth motors 630, 620 are respectively connected to the rear ends of two horizontal bars 701, 702, and threads are formed at the surfaces of two horizontal bars 701, 702.

A nut 710 screwed with the thread of the first horizontal bar 701 is fixed to the fixed body 500, so that if the third motor 630 rotates, the fixed body 500 may move forwards or rearwards along the first horizontal bar 701. Meanwhile, the first horizontal bar 701 passes through the second fixed body 800 without any disturbance, and the second fixed body 800 does not move by the rotation of the first horizontal bar 701.

As the fixed body 500 moves forwards or rearwards, the first tube body 110 and the operating device 600 coupled thereto also move forwards or rearwards together.

Similarly, a nut (not shown) screwed with the thread of the second horizontal bar 702 is fixed to the second fixed body 800, so that if the fourth motor 620 rotates, the second fixed body 800 may move forwards or rearwards along the second horizontal bar 702. If the second fixed body 800 moves forwards or rearwards, the second tube body 120 also moves forwards or rearwards.

In this configuration, the first tube body 110 and the second tube body 120 may translate in parallel independently from each other.

Figure 18:
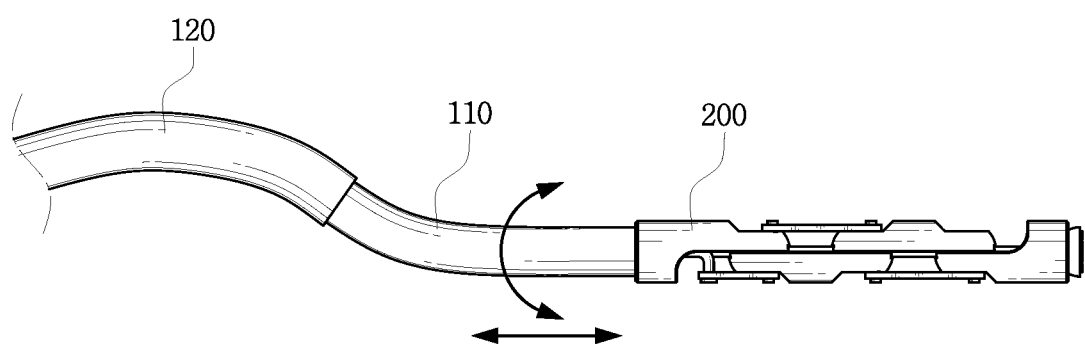
FIG. 18 is a diagram showing a front end of the active cannula of FIG. 17.

By allowing the first tube body 110 and the second tube body 120 to suitably rotate and/or translate in parallel, as shown in FIG. 18, two tube bodies 110, 120 may suitably curve according to a shape of the space into which an instrument is inserted.

The first tube body 110 curves or rotates by allowing the first tube body 110 and the second tube body 120 overlapped with each other to rotate and/or translate in parallel, and also an operation of the end-effector 300 is controlled by linearly moving the first tube body 110 in the duct 3 so that the end-effector 300 may be moved to a desired working position.

A work such as photographing may be suitably performed by using the end-effector 300 located at a desired working position.

At this time, the end-effector 300 may make two-dimensional movement in the x-z axis direction (namely, in the forward and rearward direction) by the pivotal movement of the joint structure 200, and also the end-effector 300 may change its location and direction in the y axis direction by allowing the first tube body 110 to linearly move, rotate or curve in the vertical and horizontal direction, thereby allowing three-dimensional location and direction changes.

What is claimed is:

1. An endoscope robot, which is inserted into a duct to perform a predetermined work, the endoscope robot comprising:
   a flexible first tube body;
   a joint structure coupled to an end of the first tube body; and
   an end-effector connected to the joint structure so that location and direction of the end-effector are adjusted by the joint structure,
   wherein the joint structure comprises:
   a fixed arm coupled to an end of the first tube body; and
   a plurality of pivotal arms that are pivotally connected in a series comprising a first pivotal arm, which is pivotally connected to the fixed arm, a second pivotal arm, and a last pivotal arm to which the end-effector is connected,
   wherein each pivotal arm in the series, excluding the first pivotal arm, is configured to pivot, relative to an immediately preceding pivotal arm in the series, in response to the first pivotal arm being pivoted relative to the fixed arm,
   wherein the first tube body is configured to curve and linearly move in the duct to move the end-effector to a working position, and
   wherein the plurality of pivotal arms is configured to pivot at the working position to adjust location and direction of the end-effector.

2. The endoscope robot according to claim 1,
   wherein the first tube body is rotatable based on a central axis of the first tube body in the longitudinal direction,
   wherein the end-effector is configured to move in a front and rear direction by pivoting of the plurality of pivotal arms and move in a vertical and horizontal direction by curving and rotating of the first tube body, thereby allowing three-dimensional location and direction changes.

3. The endoscope robot according to claim 1, wherein the joint structure further includes:
   a flexible rod configured to linearly move in a length direction relative to the first tube body to pivot the first pivotal arm relative to the fixed arm; and
   a plurality of link bodies for subordinating the plurality of pivotal arms to each other so that, in response to the first pivotal arm being pivoted, other pivotal arms in the series of pivotal arms are correspondingly pivoted.

4. The endoscope robot according to claim 3,
   wherein the first tube body has a hollow,
   wherein the rod extends into the first tube body,
   wherein each of the pivotal arms in the series is configured to, in response to the first pivotal arm being pivoted to a first extent with the respect to the fixed arm, pivot an extent corresponding to the first extent with respect to the immediately preceding pivotal arm in the series.

5. The endoscope robot according to claim 4, further comprising a link arm having one end pivotally connected to an end of the rod and the other end pivotally connected to the first pivotal arm,
   wherein the rod extends along a center of the length direction of the first tube body, and
   wherein the first pivotal arm is configured to pivot according to pivoting of the link arm caused by linear movement of the rod.

6. The endoscope robot according to claim 3,
   wherein each pivotal arm has a pin-shaped link connector protruding on a side of the pivotal arm,
   a corresponding link body is rotatably it onto the pin-shaped link connector, and
   each pivotal arm and the corresponding link body are fixed by riveting an end of the pin-shaped link connector protruding out of the corresponding link body.

7. The endoscope robot according to claim 1,
   wherein the plurality of pivotal arms is configured to be pivoted in the same direction.

8. The endoscope robot according to claim 1,
   wherein two pivotal arms disposed adjacent to each other are directly connected by means of a pivotal joint.

9. The endoscope robot according to claim 1,
   wherein the first tube body is a micro tube body made of a super-elastic shape-memory alloy and having a curved portion with a predetermined curvature.

10. The endoscope robot according to claim 9, further comprising a second tube body having a curved portion with a curvature different from the curved portion of the first tube body and made of a super-elastic shape-memory alloy with a greater diameter in comparison to the first tube body,
    wherein the first tube body is inserted into the second tube body, and wherein the first tube body and the second tube body overlapped with each other are configured to move relatively to change a curved shape of the first tube body so that the first tube body curves or rotates in the duct.

* * * * *